(12) United States Patent
Kelly et al.

(10) Patent No.: US 12,257,578 B2
(45) Date of Patent: Mar. 25, 2025

(54) INTEGRATED FLUID MODULE AND TEST DEVICE

(71) Applicant: ATOMO DIAGNOSTICS PTY LIMITED, Sydney (AU)

(72) Inventors: John Kelly, Sydney (AU); Huw Wallis, Sydney (AU); Keith Bocchicchio, Sydney (AU); Shing Yan Kong, Sydney (AU)

(73) Assignee: ATOMO DIAGNOSTICS PTY LIMITED, Sydney (AU)

( * ) Notice: Subject to any disclaimer, the term of this patent is extended or adjusted under 35 U.S.C. 154(b) by 0 days.

(21) Appl. No.: 18/138,532

(22) Filed: Apr. 24, 2023

(65) Prior Publication Data
US 2023/0372929 A1    Nov. 23, 2023

Related U.S. Application Data

(62) Division of application No. 16/348,979, filed as application No. PCT/AU2016/051134 on Nov. 21, 2016, now Pat. No. 11,633,733.

(51) Int. Cl.
| | |
|---|---|
| *B01L 3/00* | (2006.01) |
| *A61B 5/151* | (2006.01) |
| *A61B 5/157* | (2006.01) |
| *B29C 65/00* | (2006.01) |
| *B29C 65/18* | (2006.01) |

(Continued)

(52) U.S. Cl.
CPC ... *B01L 3/502715* (2013.01); *B01L 3/502707* (2013.01); *B29C 65/18* (2013.01); *B29C 66/72321* (2013.01); *A61B 5/15144* (2013.01);
*A61B 5/157* (2013.01); *A61B 2562/0295* (2013.01); *B01L 2200/027* (2013.01); *B01L 2200/0605* (2013.01);
(Continued)

(58) Field of Classification Search
CPC ......... B01L 3/502715; B01L 3/502707; B01L 2200/0605; B01L 2300/0887; B01L 2200/07; B01L 2200/0684; B29C 66/72321; B29C 65/18; A61B 5/15144; A61B 5/157; A61B 2562/0295; B29K 2623/06; B29L 2031/753
See application file for complete search history.

(56) References Cited

U.S. PATENT DOCUMENTS

| | | |
|---|---|---|
| 6,342,123 B1 | 1/2002 | Rees et al. |
| 8,806,842 B1 | 8/2014 | Penn et al. |

(Continued)

FOREIGN PATENT DOCUMENTS

| | | |
|---|---|---|
| WO | 2005050165 | 6/2005 |
| WO | 2014172247 | 10/2014 |
| WO | 2015075677 | 5/2015 |

OTHER PUBLICATIONS

International Search Report, mailed on Feb. 16, 2017, in PCT Application No. PCT/AU2016/051134. (14 pages).

(Continued)

*Primary Examiner* — Brian J. Sines

(57) ABSTRACT

An integrated testing device and fluid module are disclosed, as well as a method of manufacture. Fluid module contains a reservoir containing a test fluid, and a control vessel. The reservoir discharges test fluid into the control vessel, which discharges the test fluid in a controlled way to a test component.

7 Claims, 11 Drawing Sheets

(51) Int. Cl.
*B29K 623/00* (2006.01)
*B29L 31/00* (2006.01)

(52) U.S. Cl.
CPC .................. *B01L 2200/0684* (2013.01); *B01L 2300/0887* (2013.01); *B29K 2623/06* (2013.01); *B29L 2031/753* (2013.01)

(56) References Cited

U.S. PATENT DOCUMENTS

| | | | |
|---|---|---|---|
| 11,633,733 B2* | 4/2023 | Kelly | A61B 5/150343 435/6.1 |
| 2005/0026126 A1 | 2/2005 | Hageman | |
| 2006/0118434 A1 | 6/2006 | Einer et al. | |
| 2010/0179473 A1 | 7/2010 | Genosar | |
| 2012/0107811 A1 | 5/2012 | Kelso et al. | |
| 2014/0236044 A1 | 8/2014 | Kelly et al. | |

OTHER PUBLICATIONS

Written Opinion of the ISA, mailed on Feb. 16, 2017, in PCT Application No. PCT/AU2016/051134. (11 pages).

Written Opinion of the ISA, mailed on Apr. 17, 2018, in PCT Application No. PCT/AU2016/051134. (12 pages).

* cited by examiner

Start

Button Depressed/ Fluid Release

Fluid Delivered/ In Well

Blister with Well & Test Strip

Perimeter Seal Area

Unsealed Perimeter Area

Frangible Seal Area

INTEGRATED FLUID MODULE AND TEST DEVICE

CROSS-REFERENCE TO RELATED APPLICATION(S)

This application is a divisional of U.S. patent application Ser. No. 16/348,979, entitled INTEGRATED FLUID MODULE AND TEST DEVICE, filed on May 10, 2019, which claims priority to International Patent Application No. PCT/AU2016/05, filed on Nov. 21, 2016, which claims priority to Australian Patent Application No. 2016904609, filed on Nov. 11, 2016, the entirety of which is incorporated herein by reference.

TECHNICAL FIELD

The present invention relates to devices and methods for providing tests which require a test fluid, and to devices and packages which facilitate such testing.

BACKGROUND OF THE INVENTION

Various kinds of tests, for example medical tests, assays and industrial tests, are performed which enable a relatively rapid outcome to be obtained at the point of testing. These may be, for example, home tests, point of care tests, or used in laboratories, pathology clinics or hospitals.

Performing these relatively rapid tests can require complicated instructions and multiple devices and components to be used. The present invention is not concerned with the specific chemical or biochemical tests to be performed, but rather with the devices, fluid delivery and associated mechanical systems which house and contain the test components. For example, in a medical context, such devices and systems may be used with a lateral flow or other type of rapid test.

In a typical conventional home or point of care blood test, for example, the user is presented with a collection of components, including the test device itself, a separate lancet, blood collection receptacles, a container of buffer or other test fluid, an adhesive bandage, cleaning wipes, and possibly further components. The user is expected to follow a very precise sequence of steps, typically including cleaning the site, operating the lancet, obtaining a blood sample of a known volume and delivering it to the precise place required, applying a buffer solution at the right time and place and at the correct volume and rate, reading the test result and interpreting the outcome.

Many tests are performed either as infrequent or one off procedures, so that the user does not become proficient through regular use. Procedures performed at point of care are carried out generally by skilled operators, but again the complexity and dexterity required to carry out the test accurately presents a challenge and specific tests may be performed infrequently. In such situations it would be advantageous if the test device could better facilitate simple, reliable and accurate operation.

In PCT application numbers PCT/AU2011/000315 and PCT/AU2011/022321, the disclosures of which are incorporated by reference herein, the present applicant has disclosed integrated testing devices. In particular, those devices may include a reservoir or sachet of a physiologically acceptable fluid, such as a buffer. For many tests, for example certain blood tests, it is required that a buffer or other reagent is applied to the test material after the blood sample, in order to achieve a valid result or to achieve the result within an acceptable timeframe. The devices disclosed in embodiments of these disclosures permit the user to discharge a fluid, illustratively a buffer, from the internal reservoir onto the test material.

PCT publication No. WO2015075677, the disclosure of which is hereby incorporated by reference, discloses test devices and methods, in which a reservoir within the test device discharges into a control vessel, so that the rate of delivery of fluid to a test material is controlled.

It is an object of the present invention to provide a test device, fluid delivery module and method which improve the delivery of fluids to a test material.

SUMMARY OF THE INVENTION

In a broad form, the present invention provides an integrated package for delivering a test fluid, and a process for forming such a package.

According to one aspect, the present invention provides a process for forming a liquid filled reservoir with a frangible seal, the frangible seal being across a fluid conduit extending from a liquid filled reservoir, the process including the steps of: forming a reservoir body; filling the reservoir body with a liquid; positioning a base component on the reservoir body and using a set of first tools to heat seal the base component to the reservoir body, so as to create a fluid tight seal around the reservoir body, apart from a conduit; and using a set of second tools to heat seal across the conduit, wherein the heat applied by the second tool creates a frangible seal across the conduit.

The invention further includes a fluid filled module formed by the above process.

According to another aspect, the present invention provides An integrated testing device including: a test component; a test fluid module, including a reservoir containing a test fluid, a delivery vessel, and a conduit connecting the reservoir and the delivery vessel; and a fluid delivery actuator, wherein operation of the fluid delivery actuator causes the test fluid to be released from the reservoir into the delivery vessel, the delivery vessel being adapted to provide a controlled discharge of test fluid onto the test component.

According to a further aspect, the present invention provides a method for delivered a test fluid for an integrated test, including at least the steps of: providing a test unit including a test component, a fluid module having a reservoir containing a test fluid, a delivery vessel, and a conduit connecting the reservoir and the delivery vessel, and a fluid delivery actuator; operating the fluid delivery actuator and thereby exerting a pressure on the reservoir; releasing the fluid into the delivery vessel as a result of the pressure on the reservoir; thereby providing a controlled release of fluid from the delivery vessel onto the test component.

Implementations of the present invention can also, allow for different rates of release, simply by varying the size and/or shape of the opening in the vessel. The fluid may be released directly from the control vessel onto the test component, or via a conduit or channel.

The term 'controlled discharge' throughout the description and claims refers to releasing the fluid from the vessel in a way which is more controlled in flow rate than simply releasing the full contents of the sachet in a single burst. It may, in one form, merely amount to slowing down the rate of flow. It may in other forms more closely control the rate of discharge and adapt it closely to the requirements of the test. In many forms, the discharge rate will not be constant.

Implementations of the present invention accordingly allow for a convenient, accurate and practical fluid delivery module, for use in integrated testing and in other applications.

BRIEF DESCRIPTION OF THE DRAWINGS

Illustrative embodiments of the present invention will now be described with reference to the accompanying drawings, in which.

DETAILED DESCRIPTION OF THE INVENTION

The present invention will be described with reference to a number of possible embodiments. It will be appreciated that the present invention is capable of being implemented in numerous ways, in addition to the examples provided. The embodiments are intended as illustrative, and are in no way limitative of the inventive concept or its possible implementations. Further, it will be understood that the features of different embodiments may be formed into different combinations, or added together, in order to provide further implementations of the present invention.

The present invention is principally concerned with a specific aspect of the operation of a test device, relating to the discharge of a fluid which is intended to contact the test material, and to the manufacture and construction for a module for discharging a test fluid. Accordingly, while specific examples of the remaining mechanical structures of a test unit will be provided and described, it will be understood that in principle the present invention can be used with any design of such a test unit. In particular, known test units, as well as those disclosed in the specifications incorporated by reference, may be modified so as to incorporate implementations of the present invention.

Whilst the invention will be principally described with reference to a medical application, it will be appreciated that the present invention can be applied to many other forms of industrial or laboratory tests, in which a test fluid must be added to a test material, or test sample, prior to a result being determined. Other examples of possible applications include environmental testing, biosecurity, food safety, testing for illicit drugs, and veterinary medicine.

Figure 1:
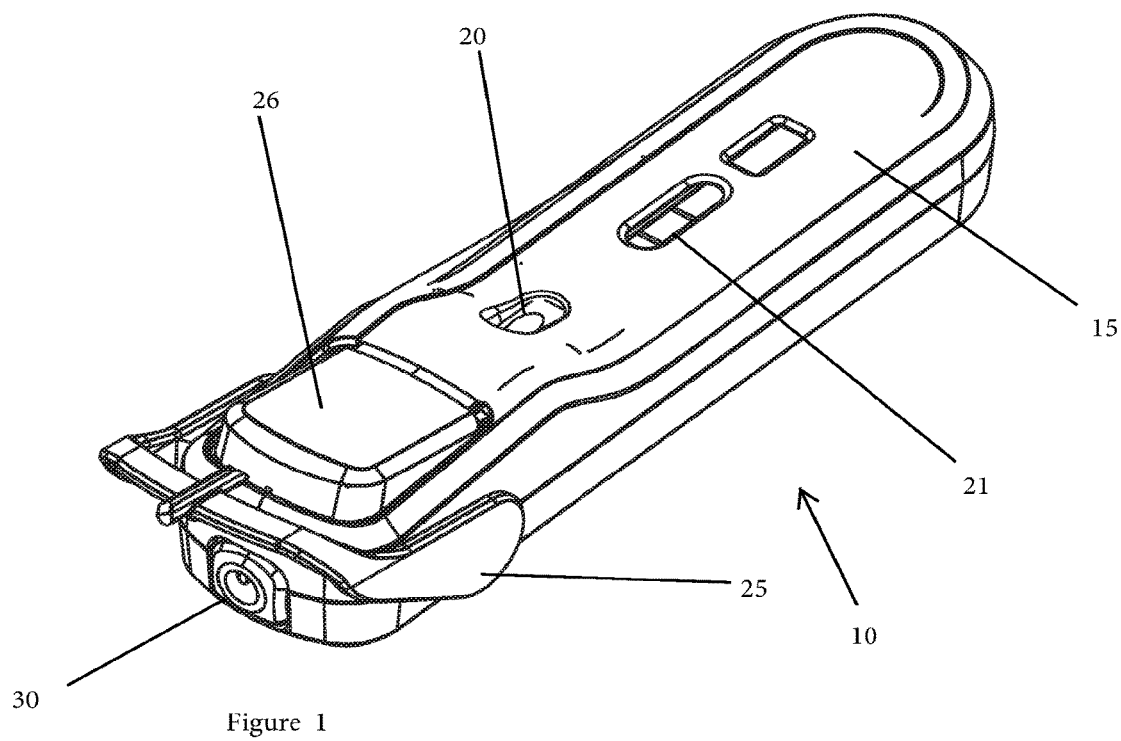
FIG. 1 shows an isometric view of an implementation of the present invention, without the lancet activated.
Figure 2:
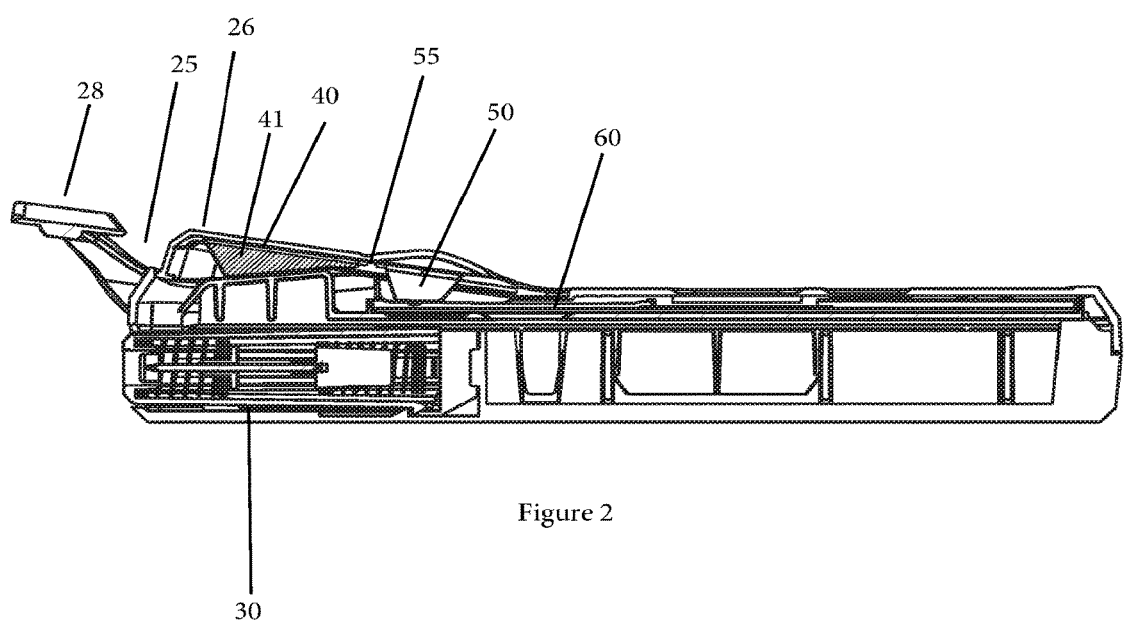
FIG. 2 is a view in section of an implementation in a first position.

FIGS. 1 and 2 illustrate one implementation of the present invention, in cross section in FIG. 2. The test unit 10 includes a cover 15, which includes a depressible portion 26 for releasing the test fluid 41. Test fluid 41 is contained in a package 40. Test unit 10 further includes an arm 25 with a collection device 28 for a bodily fluid, in this case blood. Test unit 10 also has an opening 20 for a blood sample to be received, and an indicator opening 21, through which the result of the test can be seen.

Package 40 includes a fluid reservoir 43 containing test fluid 41, a frangible seal 55, and a well 50.

Figure 3:
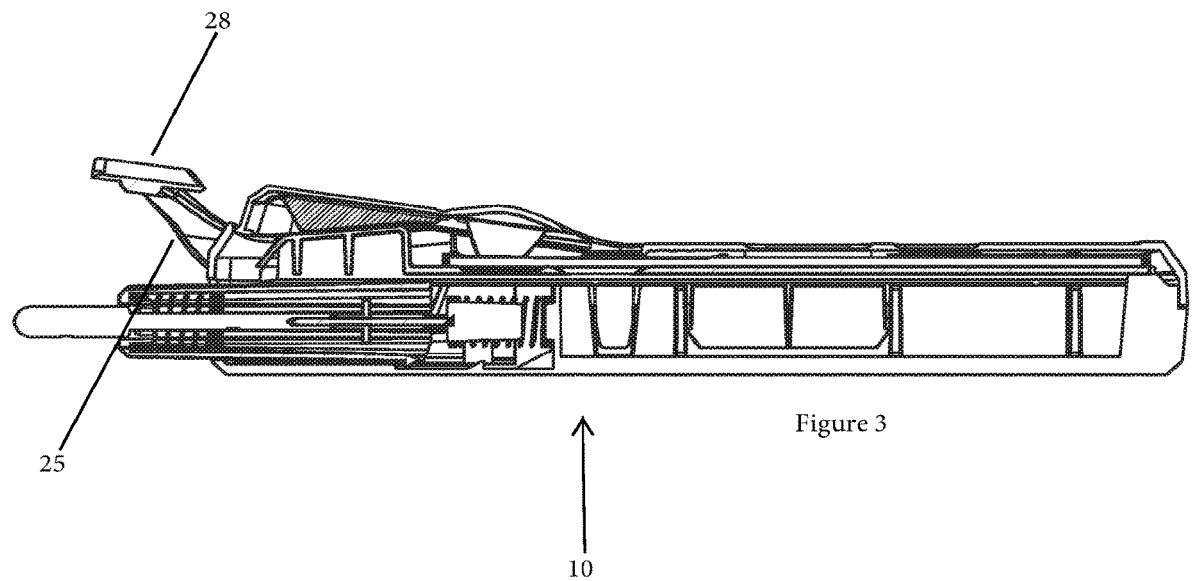
FIG. 3 is a view in section of an implementation in a second position.

As will be described in more detail below, in use, the operator according to this embodiment operates lancet 30 to release blood from a suitable site on the body, for example a finger. In this implementation lancet 30 is integrated with the unit, although in other implementations it could be a separately supplied device. Lancet 30 is spring loaded and once actuated will penetrate the user's finger. The user may need to milk the blood from the lanced site in order to provide a sufficient sample In FIG. 2, lancet 30 is ready for use, once the cover 31 is removed. In FIG. 3, lancet 30 has been operated and is then withdrawn within body 10 (for safety). The device is now ready for collection of blood. Collection device 28 is placed onto the exuded blood, and withdraws (in this case by capillary action) a sample. Other sample collection arrangements may be used in alternative implementations, for example a non-integral suction or capillary device, or direct placement of the fluid onto the test material 60. In the illustrated arrangement, collection device 28 will retain only the required volume of blood.

Figure 4:
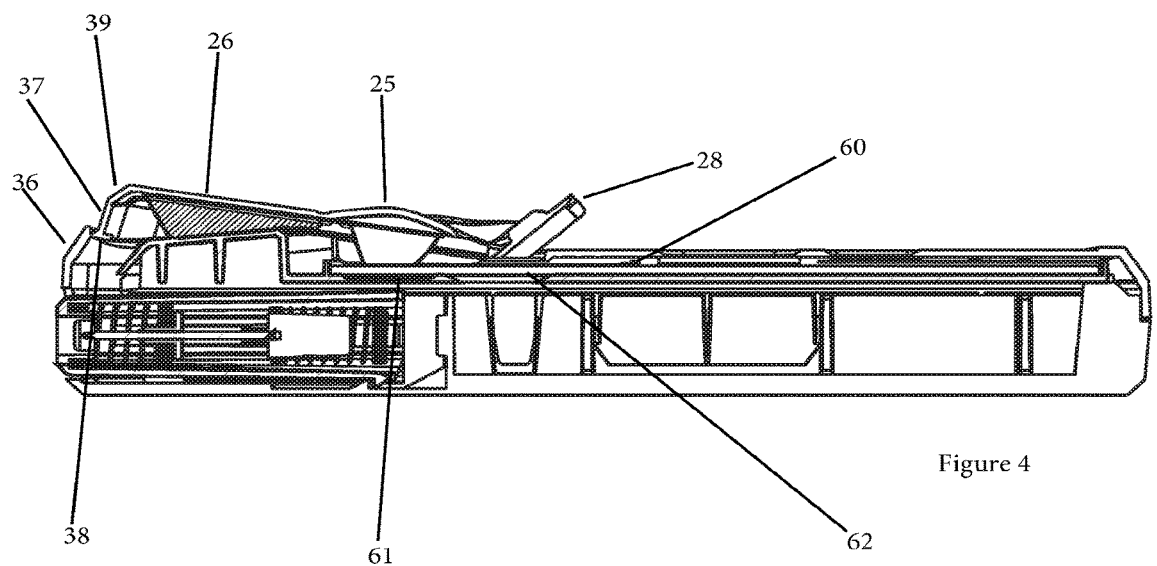
FIG. 4 is a view in section of an implementation in a third position.

After the collecting device is filled, the arm 25 may then be rotated (as will be described in more detail below) into a delivery position. The collection device is then in contact, via opening 20, with test material 60, and the sample is discharged onto test material 60. This is shown in FIG. 4.

The user may then depress section 26, which applies a force to package 40 so that the pressure in fluid reservoir 43 is increased sufficiently that frangible seal 55 fails and allows test fluid 41 to be released and flow into well 50. Well 50 has one or more openings (not shown in these views) which allow test fluid 41 to discharge at a controlled rate onto test material 60.

It is emphasised that the present invention can be applied to any kind of test, in to control the rate of test fluid introduction to the test material. In this case, the test is illustratively a lateral flow test. However, any other desired type of desired type of immunoassay, chromatographic assay, DNA assay, enzymatic assay, or other test may be used. The test may be an or use an electronic, optical or other sensor, as well as or in place of the lateral flow or similar test. The test may be read by the operator, or interpreted with an electronic or other automated system. Similarly, the test fluid may be water, a buffer solution, or any other required fluid to conduct, support or be otherwise used in conjunction with the test.

It is In other implementations, the fluid may mix with the sample to be tested prior to introduction to the test material. It will equally be understood that while the implementations illustrated show the uses of a single package. In other implementations multiple packages may be present, for example to perform multiple tests in a single unit. In yet other implementations, the package may discharge from the well onto more than one test material, for example using separate discharge openings.

Figure 5:
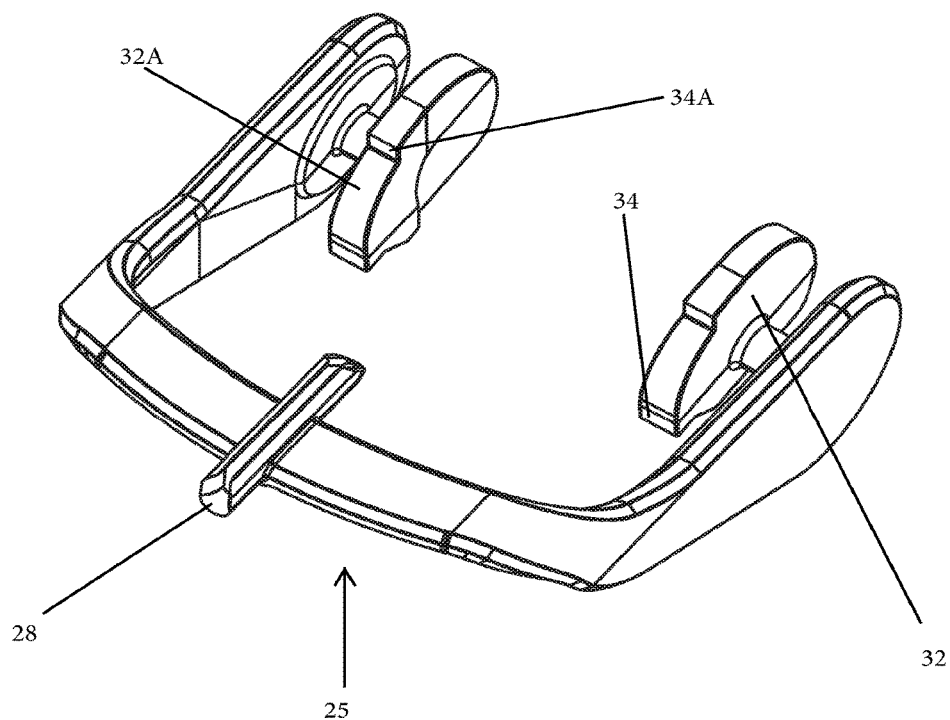
FIG. 5 is an isometric view of a blood collection arm according to one implementation.

FIG. 5 illustrates in more detail the arm 25 and associated structures. In the illustrated implementation, the arm 25 operates as an interlock to prevent the delivery of test fluid 41 onto test material 60 until the arm 25 has rotated into the delivery position.

In FIG. 5, cams 32, 32A can be seen. The rotational positon of cams 32, 32A determines whether the fluid in the reservoir can be released, via engagements with corresponding parts of the depressible portion 26.

Figure 17A:
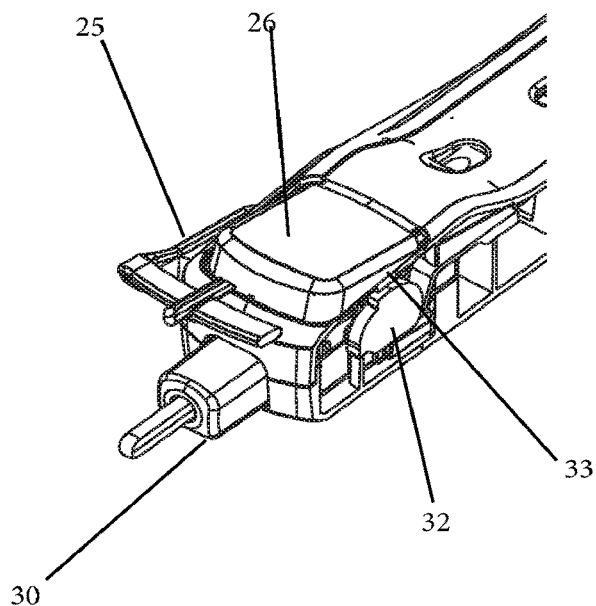
FIGS. 17A, 17B, 17C illustrate the interlock mechanism according to one implementation of the present invention.
Figure 17B:
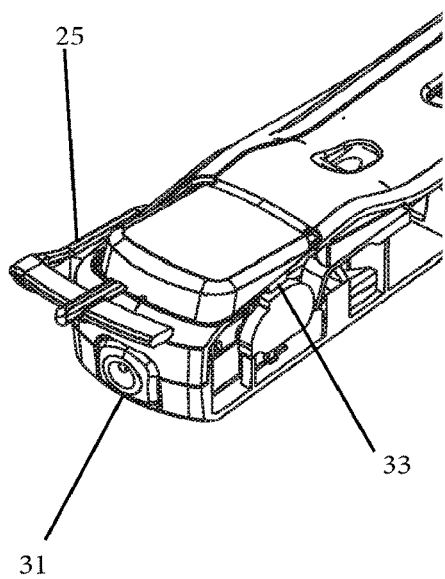

In FIG. 17A, the lancet 30 is in a rest position, and so no blood has yet been drawn. Projection 33 on depressible portion 26 is engaged by cam 32, and cannot move downwards. In FIG. 17B, the lancet 30 has been engaged and operated, and has moved to a safe rest position 31. Blood can now be collected in collection device 28. Cam 32 still blocks projection 33.

Figure 17C:
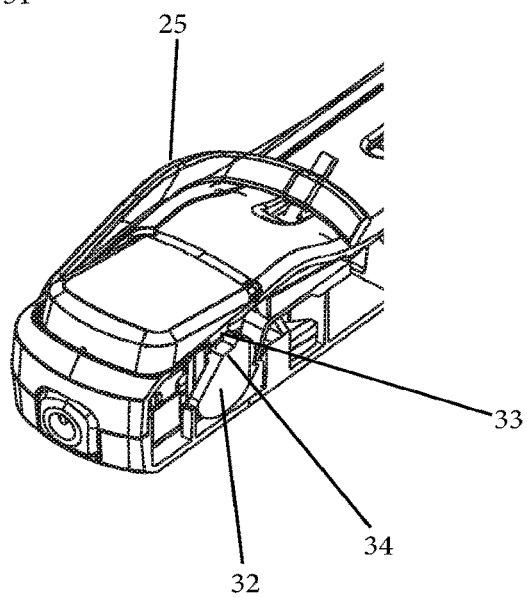

In FIG. 17C, arm 25 has been rotated, so that blood can be deposited onto the test material 60 via opening 20. Cam 32 has now rotated so that recess 34 is located adjacent projection 33, and the depressible portion 26 can now be moved downward, so as to exert pressure on package 40 and release the fluid (not shown in this view). Thus, cam 32 acts as an interlock to prevent premature release of the test fluid. It will be appreciated that other mechanical system could be used to achieve this. Examples of such mechanisms are provided in the applicant's patent applications referenced above. In many cases, the timing of the delivery of the fluid is critical to a proper result, and premature release will invalidate the test.

Figure 6:
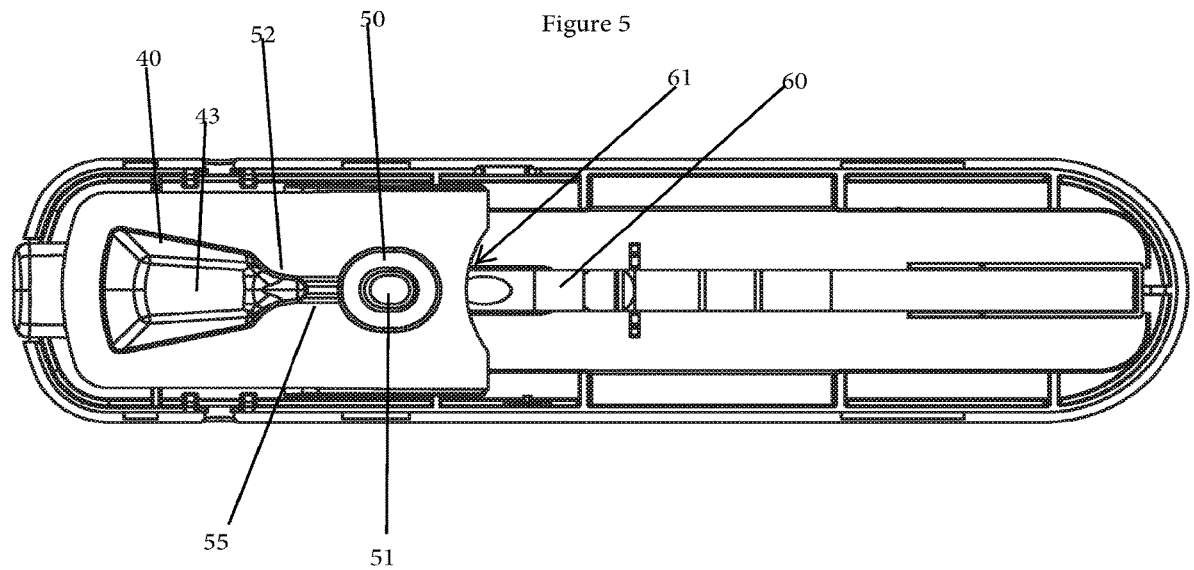
FIG. 6 is a plan view, with the upper section removed, of the implementation of FIG. 1.

The operation of the overall system, and its discharge, can be better understood from FIG. 6 and FIGS. 7A, 7B and 7C. FIG. 6 is a plan view, partly in section, so that the arrangement of the components in the fluid flow path can be better understood. Package 40 can be seen, the fluid reservoir 43 containing test fluid 41. Fluid reservoir 43 connects to well 50 through discharge conduit 52, which is initially blocked by frangible seal 55. When sufficient force is applied by depressible portion 26 to fluid reservoir 43, the frangible seal fails, fluid flows through the discharge conduit 52 into well 50. Well 50 includes a outlet 51. In this implementation, outlet 51 discharges directly onto area 61 of the test material 60. Referring to FIG. 4, it can be seen that the buffer is in this implementation discharged at point 61 so that it will pass through the area 62 where the blood sample has been deposited, so as to facilitate the test. However, it will be appreciated that by suitable relative positioning, different ordering and positioning of the test fluid and sample may be provided.

Figure 7A:
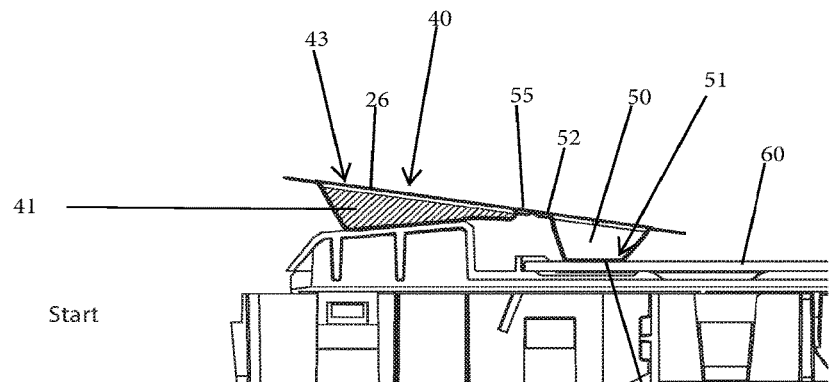
FIGS. 7A, 7B and 7C are detailed sections illustrating fluid movement within an implementation of the device.
Figure 7B:
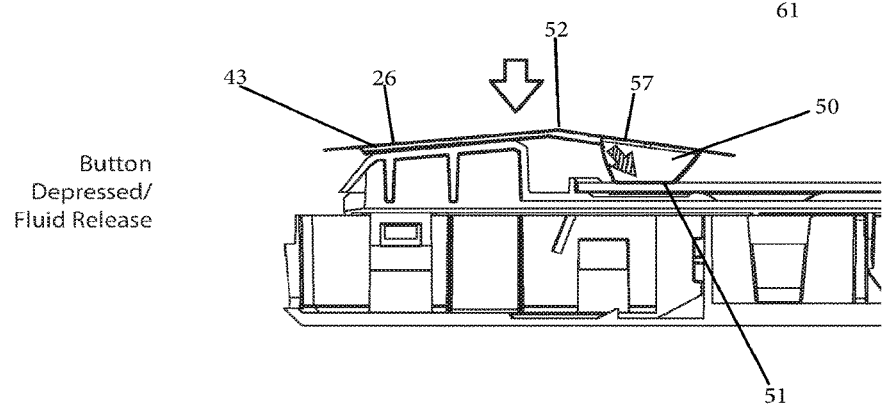
Figure 7C:
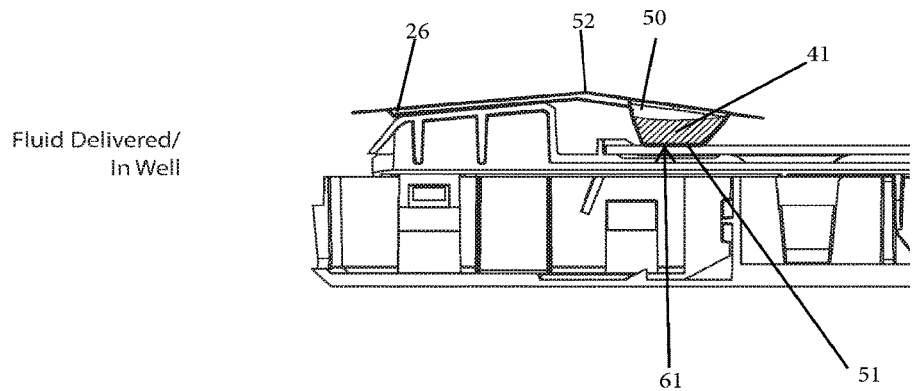

FIGS. 7A, 7B and 7C illustrate in more detail the sequence of test fluid discharge in the illustrative device.

In FIG. 7A, the fluid delivery reservoir 43 contains the test fluid 41 and has yet to be discharged by pressure from depressible portion 26. This is the condition in which the test device is supplied, and in this state, test fluid 41 is completely sealed by frangible seal 55 within the fluid delivery reservoir, thereby maintaining a desired composition and condition of the test fluid.

In FIG. 7B, depressible portion 26 has been depressed, so that the fluid reservoir 43 has been effectively emptied through conduit 52 and test fluid 41 is being discharged (as illustrated by the arrow 57) into well 50. Well 50 is directly engaged with test material 60 at area 61. It will be appreciated that in other implementations, different fluid flow paths and geometry could be employed.

However, it has been determined by the inventors that using a direct discharge and minimising the intervening fluid paths minimises the volume of fluid which remains in the fluid path, through surface effects, surface tension, and other fluidic adherence to the surfaces in the fluid path. Whilst this is not essential, minimising these losses permits a more accurate volume of test fluid to be delivered, and minuses waste.

In FIG. 7C, the test fluid 41 is discharging in a controlled way through opening 51 onto test component 60. Thus, test fluid 41 is discharged in a measured, controlled way onto test component 60 and not in an uncontained rush. Thus, well 50 acts as a control vessel, and allows for the rate of flow of test fluid 41 to be controlled.

It will be understood that while the fluid will discharge over time, it will not necessarily be at a constant rate. The rate will be determined in part by the sizes of the opening (or openings) in the well, as well as the absorption by the test material. Flow may slow as more or most of the fluid has left the vessel, for example.

It has been determined by the inventors in preferred implementations, it is advantageous for the volume of the well to be smaller than the than the volume of the fluid reservoir. This allows of the depression of the depressible portion 26 to exert force over a period of time, so as to provide a positive pressure from the fluid 41 in the fluid reservoir 43, through well 50, outlet 51, and into the test material at area 61. This in turn provides for a consistent flow of test fluid 41 into the test material 60. This also more positively forces the fluid into the test material. Test material 60 in this implementation draws test fluid 41 into and along the test material 60, by capillary action, so that further fluid can be drawn in from well 50 and ultimately from reservoir 43.

It will also be understood that the fluid should contact the test material as directly as possible, and that it is desirable that the volume of test fluid 41 can be controlled to provide consistent delivery volumes, as well as a consistent and correct total volume delivered. This is facilitated by the volume of well 50 being smaller than the volume of reservoir 43. As will be described in more detail below with reference to FIG. 11, a vent opening 111 is advantageously provided in the seal over well 50, 102. If no vent is provided, air cannot enter to replace the test fluid 41 as it is dispensed onto test material 60. This in turn may create a pressure lock, preventing or impeding the passage of test fluid 41 onto test material 60, or fluid delivered outside of the test material due to pressure build up behind the delivered fluid, exiting the well.

Vent opening 111 also assists in another respect. In some circumstances the user may apply pressure sufficient to excessively compress reservoir 43. This can then result in an uncontrolled rapid burst of fluid 'exploding' inside teste unit 10, so the fluid is delivered to the interior in general and not in the desired controlled way to the test material 60. Vent opening 111 in this case provides a way for excess fluid pressure to vent, without the whole fluid reservoir 43 failing.

To facilitate the flow, it is advantageous that is there is a good fluid engagement between the outlet 51 and area 62. If the engagement is loose, then test fluid 41 may be discharged within the device but not on test material which is undesirable.

In this implementation, a further feature is that an interlock is provide between the depressible portion 26 and the test unit, so that once actuated the depressible portion stays in the depressed position and the reservoir 43 compressed.

Referring first to FIG. 4, the test strip unit 10 incudes a front projection 36. This is located just in front of the depressible portion 26. Depressible portion 26 also includes a lower projection 37 with a foot 38 at the base, and angled face 39.

Figure 6A:
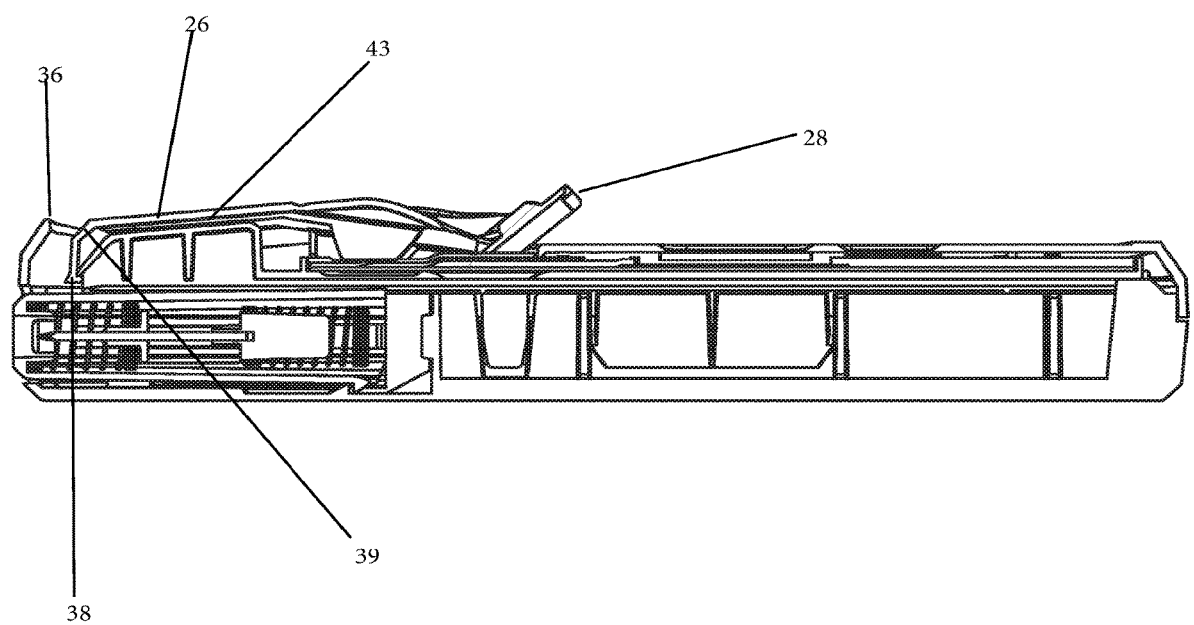
FIG. 6A illustrates the situation after the depressible portion has been actuated.

FIG. 6A illustrates the situation after the depressible portion 26 has been actuated. The fluid has been forced, or is in the process of being forced, from reservoir 43 into well 50. Foot 38 has been forced past the top edge of projection 36, and projection 36 now engages angled face 39. Thus, depressible portion 26 is now retained in the depressed state, thereby maintaining pressure on reservoir 43. This retention also prevents any chance that fluid could return into the reservoir, or that the force to maintain pressure on the reservoir and hence force fluid through well 50 and into test material 60 will not be maintained. As such, this interlock feature assists in ensuring controlled delivery of fluid to the test material 60.

Further, it is desirable that there be as little air within the fluid reservoir as possible. This allows for the force applied by the user via depressible portion 26 to act directly on the test fluid, when depressible portion 26 is engaged, rather than first compressing air within the package 40. Reducing the air content inside the sealed reservoir 43 reduces the burst force which the use needs to apply to release test fluid 41. A smaller burst force is desirable from a usability perspective, as it is easier for the user to operate and control. A larger burst force means that the user has to press harder which may be physically difficult in some cases, as well as increasing the risk of inadvertent damage to the test unit, or uncontrolled test fluid discharge due to excessive force. This similarly allows for more reliable operation of the package, and thus the overall device.

The fluid in the sachet may be any kind of fluid necessary or desired to perform, assist or validate the test. It will be appreciated that the fluid may have different properties, for example density, viscosity and surface tension, and that appropriate changes to the package may need to be made. The present invention is concerned with how the fluid is delivered, and is applicable to any desired fluid for use with a test.

The test material may be, illustratively, a lateral flow test for a component of blood, electrolyte, blood sugar, cholesterol or any other blood component. It may adapted to detect specific biological or immunological responses, for example the presence of a pathogen or antibodies to a pathogen. Any kind of test on a body fluid which is suitable for this type of test unit can be used. The present invention is not specific to any type or form of test material, whether of lateral flow type or otherwise. Similarly, it is not constrained to blood, but could be applied to tests on any suitable bodily fluid, for example urine, interstitial fluid, faeces, or sputum, whether directly applied to the test unit or after pre-processing. The present invention may be applied also to other chemical and biochemical tests, for example in industrial, laboratory or other applications.

It will be appreciated that the specific dimensions, shapes and parameters will need to be determined, in part by trial and error, for specific applications. The required volume of fluid will determine the size of the fluid reservoir. The properties of the specific fluid, and the required rate of flow will determine the size and nature of the outlets required in the well. The surface properties of the interaction between the specific fluid and the materials over which it will flow also need to be considered. For example, in an aqueous fluid, given the relatively high surface tension, smooth shapes are preferred over corners to ensure a smooth flow of the fluid. The well 50 illustrated is contained wholly within the test unit, however, it will be appreciated that this could be partly open if desired. The required flow rate and volume are specific to the particular test material being used, and will generally be advised by the test material manufacturer.

Figure 8:
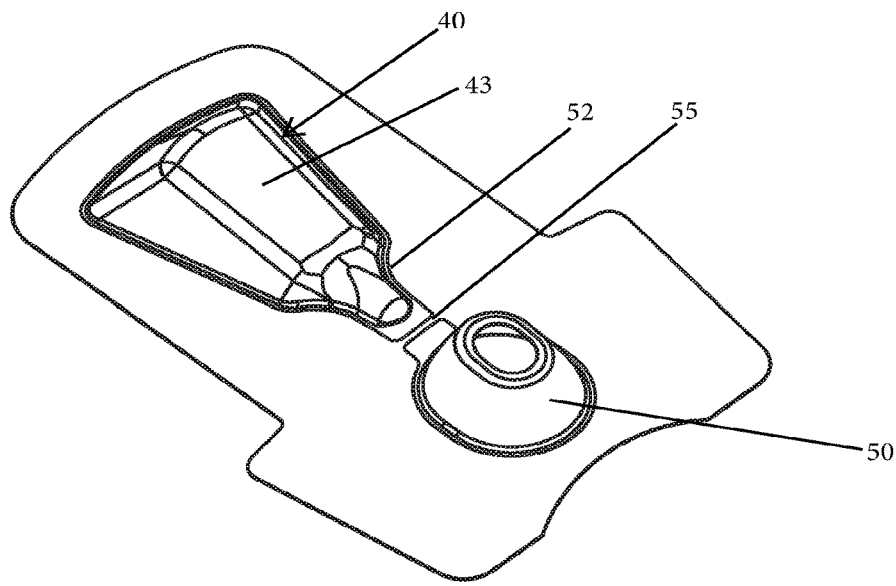
FIG. 8 illustrates an implementation of the package in a filled state.
Figure 8:
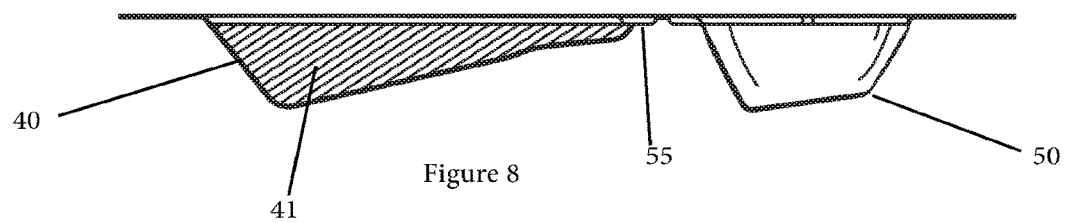

FIG. 8 illustrates one form of package 40 according to the present invention. It includes reservoir 43, containing test fluid 41, connected by conduit 52 to well 50. In FIG. 8, the package 40 is filled with test fluid. As can be seen in the sectional view, there is little or no air within reservoir 43. Frangible seal 55 provides a seal for reservoir 43, until such time as fluid release is required.

Figure 9:
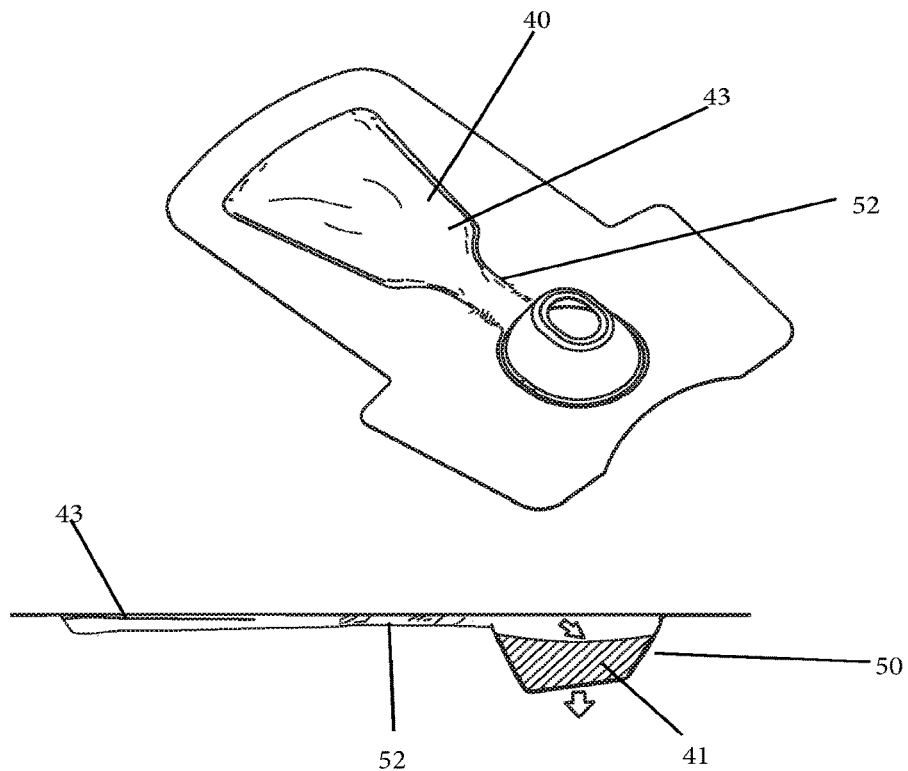
FIG. 9 illustrates an implementation of the package in an emptied state.

FIG. 9 illustrates the device of FIG. 8, after the test fluid 41 has been discharged into the well 50. Hence, reservoir 43 has now been substantially emptied. Force applied to reservoir 43 has raised the pressure in the test fluid 41 so that frangible seal 55 has failed, and test fluid 41 has passed through conduit 52 into well 50. Fluid 41 is then discharged at a controlled rate from well 50, as can be seen from the arrows in FIG. 9. It is noted that for clarity, the perspective view is upside down relative to the sectional view.

Figure 10:
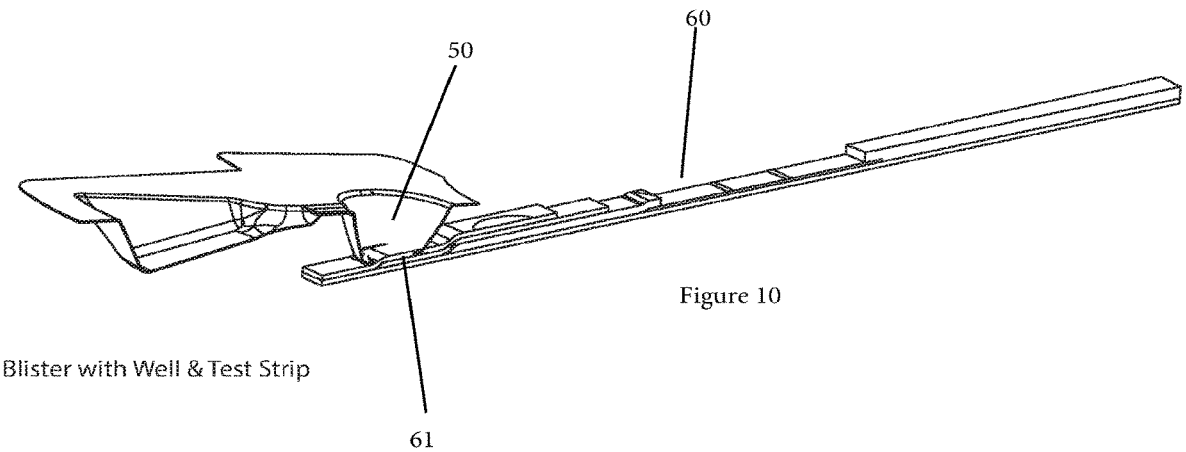
FIG. 10 is a detailed view illustrating the relationship between the well and the test strip in one implementation.

FIG. 10 illustrates only the package 40 and well 50, relative to test strip 60. The direct engagement of well 50 with test strip ensures that test fluid 41 is discharged onto the required location 61, with a minimal risk of fluid loss.

Figure 11:
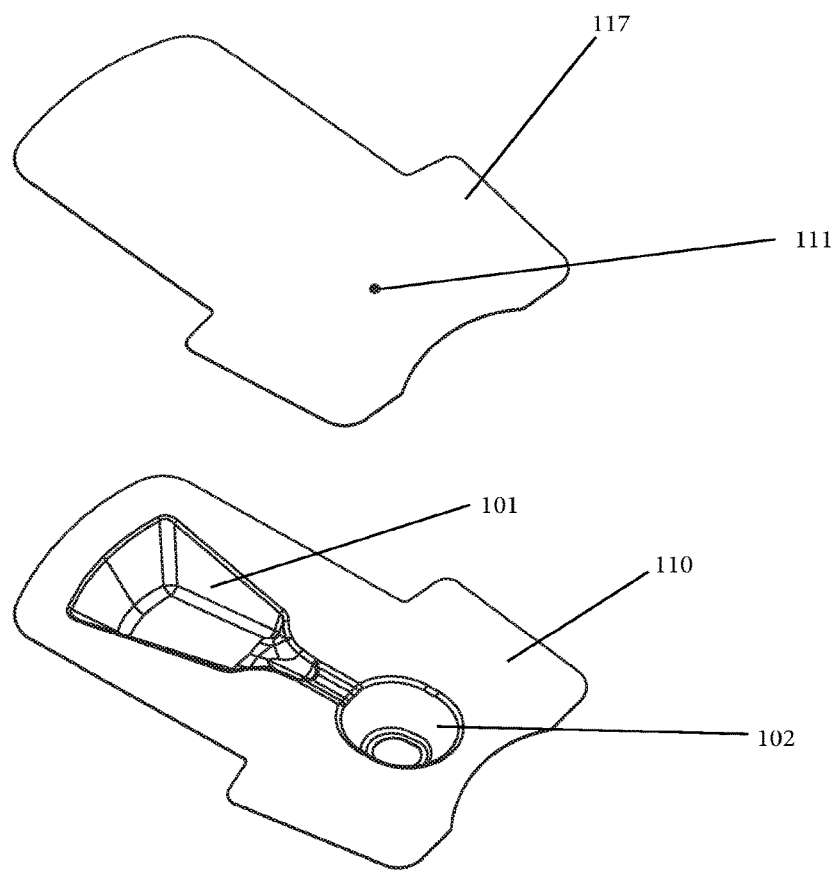
FIG. 11 illustrates the components of an implementation of the package.

FIG. 11 illustrates the components of a package prior to assembly according to one implementation of the present invention. The empty blank parts to form the upper seal 117 and body 110 of the package are shown. Prior to sealing, the reservoir recess 101 must be filled with the required test fluid 41 (not shown in this and following views for clarity). The well structure 102 and vent opening 111 are also visible.

It will be understood that the sachet or reservoir may be provided using any suitable technology. However, the following discussion relates to formation of package 40 using a heat sealing approach using multilayer materials.

The package may be formed from any suitable material. It will be appreciated that the material must be compatible with the fluid, and be inert with respect to the fluid. A heat sealed foil polymer is preferred. The polymer provides heat sealing, and the foil layer assists with protection and conservation of the fluid. It will be appreciated that in the present application fluid volumes are small, and high impermeability of the packaging is important for shelf life and retention of appropriate fluid properties.

For aqueous buffer solutions, a suitable material for the top seal is a peelable foil laminate, product code RFA 037, available commercially from Amcor Flexibles. This is a heat sealable material with layers of PET, adhesive, aluminium, and polyethylene. The material has a nominal thickness of about 60 μm.

A suitable material for the base (reservoir and well) is a cold formable laminate Formpak 3-ply, product code 13355, available from Amcor Flexibles. This is a cold formable material with layers of aluminium, OPA and PE, with a nominal thickness of about 100 μm.

The following discussion relates particularly to the application of the present invention to packages containing a small fluid volume, typically in the range of about 50 to 250 µl, and typically about 200 µl.

In general terms, the preferred manufacturing process is to form the upper seal 117 and body 110 from suitable material, then to heat seal them together, and form the frangible seal 121 by a secondary heat sealed section. It has been determined that it is impractical to do this using a single process. The frangible seal must have a well-controlled strength. The preferred material for the body 110 includes a foil layer, which has been found to conduct heat beyond the desired confines of the seal. As a result, this approach does not produce a well formed seal.

Figure 13:
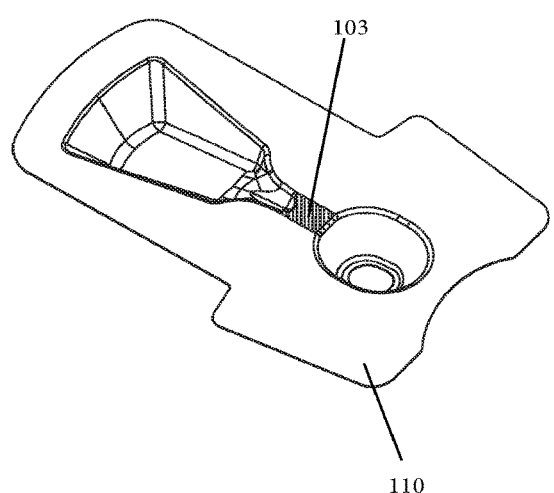
FIG. 13 illustrates the unsealed are resulting from FIG. 12.
Figure 14:
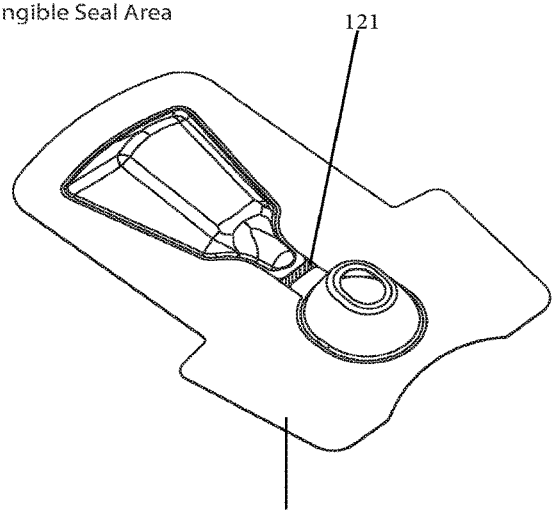
FIG. 14 illustrates a second stage in the production of an implementation of a package.

The inventors have adopted a preferred two stage manufacturing process. In this process, a perimeter seal is first formed, identified as 120 in FIG. 12. This does not seal the frangible seal, but rather the external periphery of the package 110. As can be more clearly seen in FIG. 13, region 103, which will form the fluid conduit and seal in the finished product, are not sealed. In a second stage, a relatively narrow secondary seal 121 is formed, as illustrated in FIG. 14.

A further aspect has been identified by the inventors. Even in the two stage process, there is possible heat transfer through the foil, so that some degree of sealing occurs in the conduit region. This is largely because it is very narrow, and the distance from the heated tool to the area which is not desired for sealing in the first stage is small. It is important that heat transfer is prevented between the top and bottom layers in the first stage in order to achieve a reliable seal in the second stage. If the conduit area is sealed in the first stage, the quality of the seal and its parameters cannot be properly controlled, and hence the burst force of the seal cannot be reliably controlled or predicted. This is addressed by two separate improvements.

It will be appreciated that a seal can only be created between the top and bottom layers if they are in contact, and heated. Heat causes activation of the sealing layer, in this example a PE layer, and thus potentially creates an uncontrolled seal.

In one aspect, the conduit area is formed with a larger curvature, so that the surfaces around the conduit are not in contact and so less liable to unwanted heat transfer which may cause sealing of the conduit area. It will be understood that in alternative designs, the modifications to the shape of the conduit could be to the seal, body, or both.

In a second aspect, the tool is formed not merely with an opening around the conduit part, but with an open section, so as to further reduce the unwanted heat transferred by conduction or radiation to the conduit section to eliminate any sealing of the conduit area. This cooperates with the physical gap between the layers created by the first aspect, to effectively remove the possibility of heat transfer while the layers are in contact, and hence prevents sealing of the conduit in the first stage.

Figure 15:
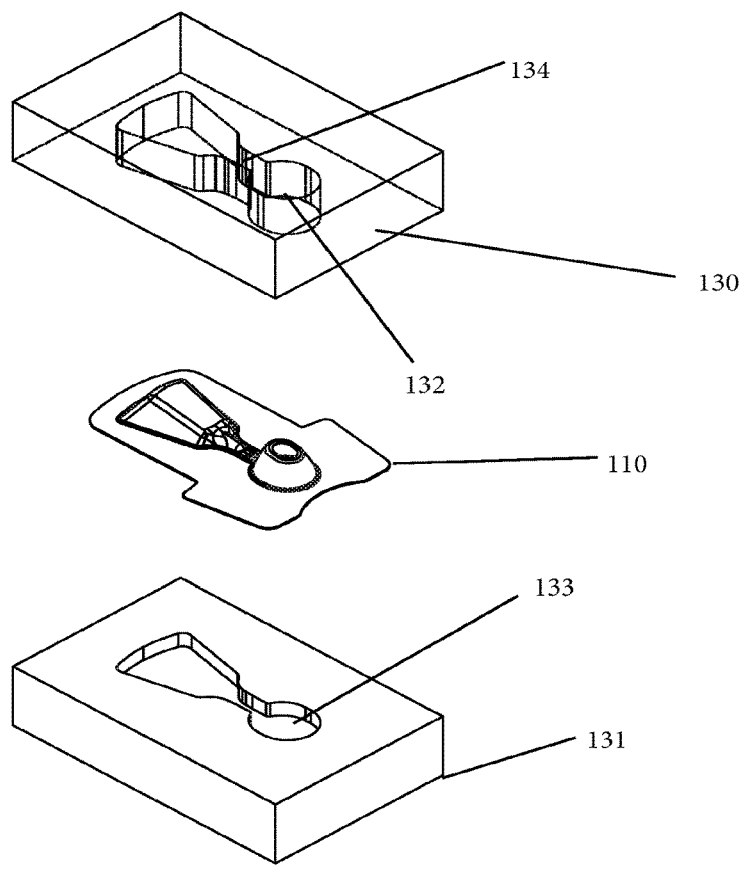
FIG. 15 illustrates notional tools for heat sealing the implementation of FIG. 12 in the first stage of sealing.

This can be seen in FIG. 15. It will be appreciated that the external dimensions of the tool will be dictated by the machine with which it is designed to be used, and so these are shown purely in a schematic way. It will further be appreciated that while a single cavity is shown, multi-cavity tools may be used following the general principles outlined.

Figure 12:
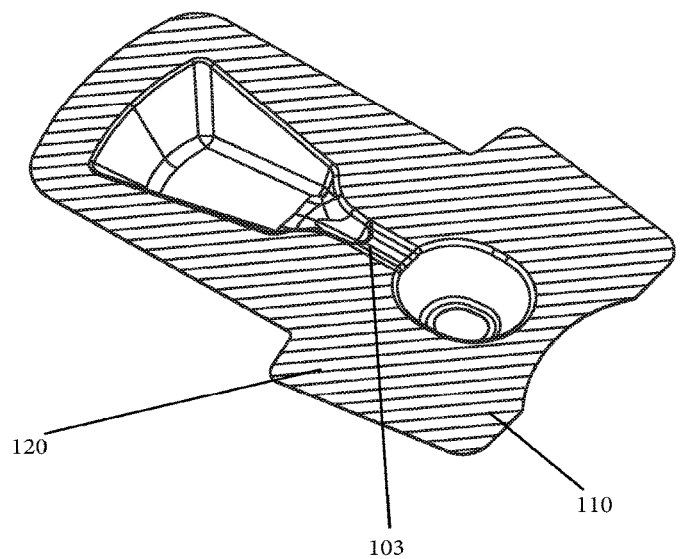
FIG. 12 illustrates a first stage in production of an implementation of a package.

The components of package 110 (the seal is not readily visible, but is of course present) are positioned so that upper tool 130 and power tool 131 are able to be moved into an operative position, generally abutting the package 110. It can be seen that the upper tool includes a recess 132 which defines the non-sealed area, and that this recess is open 134 at the top. A similar arrangement is present in recess 133 in lower tool 131. Thus, these tools cooperate to move into contact, heat the material of the package components, and produce a seal such as is shown in FIGS. 12 and 13. That is, the frangible seal 121 has not been formed.

Figure 16:
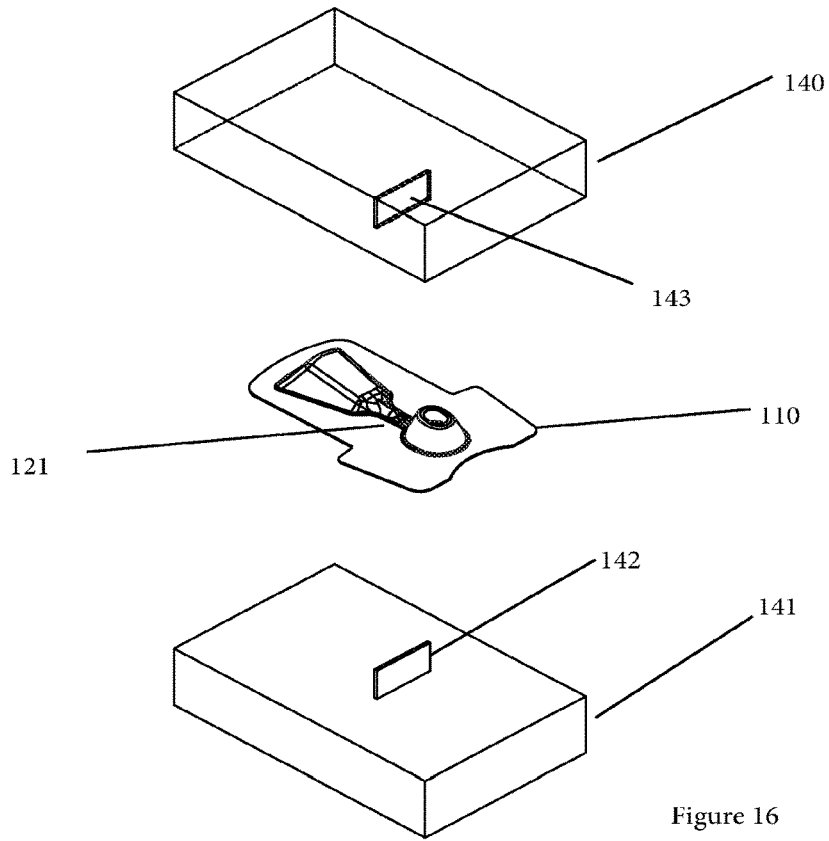
FIG. 16 illustrates notional tools for heat sealing the implementation of FIG. 14 in the second stage of production.

FIG. 16 illustrates the second stage in manufacture of the package according to this implementation. Upper tool 140 and lower tool 141 include respective blade type portions 142, 143. When there are moved into position, they form a relatively narrow seal by heat sealing the respective portions of the package, so as to provide frangible seal 121.

It will be appreciated that while the package, and its sub-components, have been illustrated having a particular shape which is operable with the mechanical systems described, for different systems and applications it would be expected that the shapes, volumes, sizes, and so forth would vary to suit the particular actuation arrangements for the package.

Figure 18A:
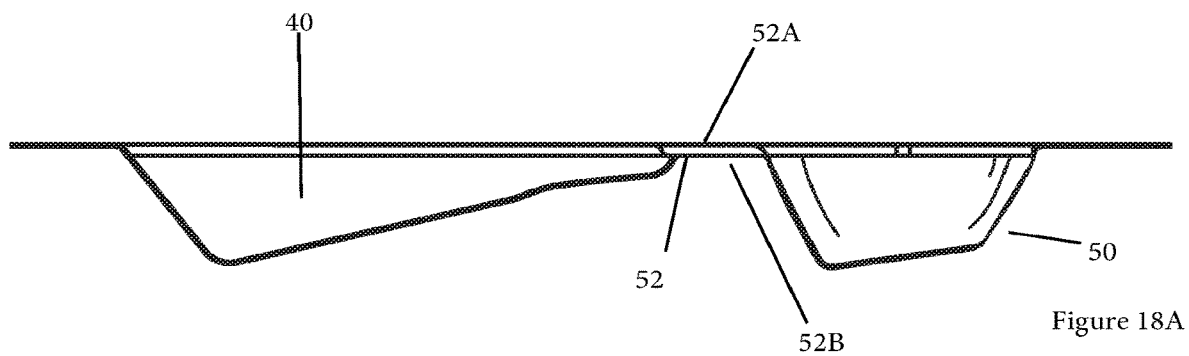
FIGS. 18A, 18B and 18C are sectional views illustrating the formation of the frangible seal.
Figure 18B:
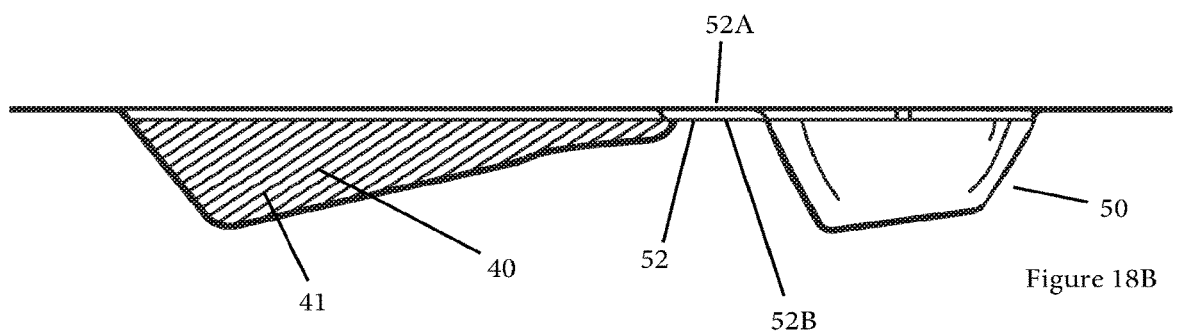
Figure 18C:
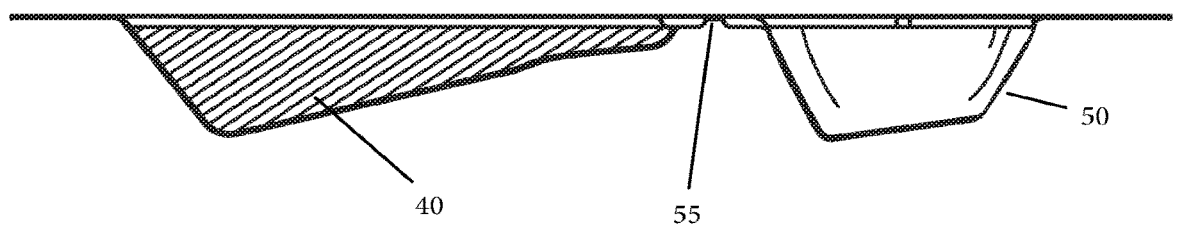

FIGS. 18A, 18B and 18C illustrate the stages of sealing discussed above, using a longitudinal cross-section. In FIG. 18B, the reservoir 40 and well 50 can be seen, before fluid is added to reservoir 41. A discharge conduit 52 is defined between layers 52A, 52B, which as discussed above in use will facilitate fluid transfer to well 50.

In FIG. 18B, fluid has been added, and the peripheral seal has been completed, but conduit 52 remains open and the surfaces 52A and 52B remain separated. In FIG. 18C, frangible seal 55 has been formed by the blades 142, 143 (not visible in this view). Thus, the layers 52A, 52B are forced together and the seal formed as part of the same process step.

This implementation accordingly allows for the rate of delivery of a test fluid to be closely controlled. The fluid is first released into the well. The size, number, and shape of the outlets, as well as the shape of the well, will determine the rate (whether variable or constant) at which the fluid is released. The interaction with the rest of the package, the pressure applied by the depressible portion, and the overall fluid flow path will influence the flow rate. For example, if the outlets are relatively small, the fluid will be released over a longer time period. The combination of controlling the volume of the fluid, and its fluid path, allows for relatively accurate control of the delivery of the fluid, and further ensures that it is delivered to the correct point on the test material.

The present invention may be implemented in ways that do not incorporate all of the preferred features noted in relation to the implementation above. The various aspects of the invention described have advantages without incorporating all the components of the described implementations. For instance, the sample of blood or other fluid could be placed directly into a suitable recess or opening in the test unit, without using the sample delivery arm or another mechanism. The package may be inserted by a user into the test unit rather than being integral.

It will be understood that the illustrative embodiments are only provided by way of example, and many other structures could be used to implement the invention. For example, the package described could be utilised with different mechanical structures than those described, and used for completely different applications to those discussed.

What is claimed is:
1. A liquid package, comprising:
   a base component;

a reservoir body, the reservoir body being heat sealed to the base component using a set of first tools to provide a reservoir; and a fluid conduit having a frangible seal to prevent egress of fluid from the reservoir and through the fluid conduit, the frangible seal being created from heat applied by a separate set of second tools across the fluid conduit.

2. The liquid package of claim 1, wherein the liquid package is configured to allow liquid to be discharged through the frangible seal when a sufficient force is applied to the reservoir.

3. The liquid package of claim 2, further comprising a discharge vessel at one end of the fluid conduit, the liquid being discharged into the discharge vessel.

4. The liquid package of claim 3, wherein the delivery vessel includes at least one outlet and is shaped and configured to deliver a controlled delivery of liquid through said outlet.

5. The liquid package of claim 1, wherein the liquid package is adapted to deliver a test fluid for use in a test.

6. The liquid package of claim 5, wherein the liquid package is adapted for use in a test unit, the liquid being discharged by a force applied by operation of the test unit so that the test fluid is delivered to a test component within the test unit.

7. The liquid package of claim 5, wherein the test is a medical test carried out on a bodily fluid or material.

\* \* \* \* \*